United States Patent
Feng et al.

(10) Patent No.: US 12,096,919 B1
(45) Date of Patent: Sep. 24, 2024

(54) INTEGRATED URINE ANAEROBIC COLLECTION AND CULTURE APPARATUS

(71) Applicant: NANJING MEDICAL UNIVERSITY, Jiangsu (CN)

(72) Inventors: Ninghan Feng, Jiangsu (CN); Hao Lin, Jiangsu (CN); Zhenyi Xu, Jiangsu (CN); Yifan Tang, Jiangsu (CN); Fengping Liu, Jiangsu (CN)

(73) Assignee: NANJING MEDICAL UNIVERSITY, Nanjing (CN)

( * ) Notice: Subject to any disclaimer, the term of this patent is extended or adjusted under 35 U.S.C. 154(b) by 0 days.

(21) Appl. No.: 18/623,033

(22) Filed: Apr. 1, 2024

(30) Foreign Application Priority Data

Dec. 12, 2023 (CN) .......................... 202311701628.X

(51) Int. Cl.
*A61B 10/00* (2006.01)
*A61M 25/00* (2006.01)
*C12M 1/00* (2006.01)

(52) U.S. Cl.
CPC ........... *A61B 10/007* (2013.01); *C12M 43/00* (2013.01); *C12M 45/05* (2013.01); *A61B 2217/005* (2013.01); *A61M 2025/0008* (2013.01); *A61M 2025/0078* (2013.01); *A61M 2025/0079* (2013.01)

(58) Field of Classification Search
CPC ............ A61M 25/0017; A61M 25/003; A61M 25/0068; A61B 10/007
See application file for complete search history.

(56) References Cited

U.S. PATENT DOCUMENTS

2019/0038451 A1  2/2019  Harvie

FOREIGN PATENT DOCUMENTS

| | | |
|---|---|---|
| CN | 204972655 U | 1/2016 |
| CN | 106474579 A | 3/2017 |
| CN | 206248395 U | 6/2017 |
| CN | 110628867 A | 12/2019 |
| CN | 215961738 U | 3/2022 |
| CN | 218853305 U | 4/2023 |
| CN | 219495770 U | 8/2023 |
| WO | 2017070155 A1 | 4/2017 |

OTHER PUBLICATIONS

Notice of Allowance of counterpart Chinese Patent Application No. 202311701628.X issued on Jan. 18, 2024.
Search Report of counterpart Chinese Patent Application No. 202311701628.X issued on Jan. 5, 2024.

*Primary Examiner* — Leslie R Deak

(57) ABSTRACT

Disclosed is an integrated urine anaerobic collection and culture apparatus, comprising: a catheter, at a front end of which a circular arc-shaped guide part and a first through hole are arranged, where a piston part is arranged inside the front end of the catheter; a first branch tube and a second branch tube, which are connected with the catheter, the first branch tube is connected with a first negative pressure vessel, and the first branch tube and the second branch tube are respectively provided with a first valve and a second valve; an aseptic centrifuge tube, which includes a tube body and a first cover body, where the first cover body is provided with a first check valve and a second check valve; a second negative pressure vessel. The present disclosure can realize the whole anaerobic operation of urine collection and culture in the bladder.

6 Claims, 2 Drawing Sheets

INTEGRATED URINE ANAEROBIC COLLECTION AND CULTURE APPARATUS

CROSS REFERENCE TO RELATED APPLICATIONS

The present application claims the benefit of Chinese Patent Application No. 202311701628.X filed on Dec. 12, 2023, the contents of which are incorporated herein by reference in their entirety.

FIELD OF TECHNOLOGY

The present disclosure relates to an integrated urine anaerobic collection and culture apparatus, and belongs to the technical field of urine collection and culture.

BACKGROUND

Research over the past decade has shown that bacteria also exist in a bladder of a human body. For example, Alan J. Wolfe's team found in 2012 that for bladder urine collected by suprapubic needle aspiration of bladder, the presence of bacteria in the bladder could be detected either by Enhanced quantitative urine culture (EQUC) or by a 16S rRNA high-throughput sequencing method. Since then, there have been many other studies at home and abroad with similar findings. Moreover, researchers also found that bladder microecology can be used to reveal the health of a urinary system.

Human microecological research, following cross-sectional observational studies, usually requires the use of culture techniques to isolate the bacteria, identify them, and then observe the function of these bacteria on the host by planting the bacteria in experimental animals, so as to determine whether these bacteria are probiotic or pathogenic.

According to sequencing results, 80% of the bacteria in the bladder are anaerobic bacteria. Currently, urine is often collected from the bladder using a catheter, then injected into an aseptic centrifuge tube, and then cultured. During this process, due to the exposure of urine to the air, strict anaerobic bacteria are very easy to die, so they cannot be cultured, and follow-up animal transplantation experiments cannot be carried out.

SUMMARY

The present disclosure aims to provide an integrated urine anaerobic collection and culture apparatus to solve the technical problem that it is difficult to realize an anaerobic operation in the process of collecting and culturing urine in a bladder in the prior art, resulting in the death of anaerobic bacteria.

The present disclosure adopts the following technical scheme: an integrated urine anaerobic collection and culture apparatus, wherein the apparatus comprises a catheter, a front end of the catheter is used to insert into a bladder, a middle and back end of the catheter is connected with a first branch tube and a second branch tube, the front end of the catheter is provided with a circular arc-shaped guide part, the front end of the catheter is provided with a first through hole communicated with the interior thereof, a piston part is arranged inside the front end of the catheter, the piston part is used to seal the first through hole, an end of the piston part near the guide part is in contact with the guide part, so that the front end of the piston part is sealed with the guide part with no gap therebetween, an outer circumference of the piston part is fitted with an inner wall of the catheter in a sliding seal manner, an end of the piston part away from the guide part is connected with a traction rope, and the traction rope passes through a back end of the catheter; the first branch tube and the second branch tube are internally connected with the catheter, and a connection position of the second branch tube and the catheter is located upstream of a connection position of the first branch tube and the catheter, the first branch tube is connected with a first negative pressure vessel, the first branch tube and the second branch tube are respectively provided with a first valve and a second valve; the second branch tube is connected with an aseptic centrifuge tube, the aseptic centrifuge tube comprises a tube body and a first cover body, wherein the first cover body is provided with a first check valve and a second check valve, the first check valve is connected with the second branch tube, the direction of the first check valve is from the second branch tube to the inside of the tube body, the second check valve is connected with a second negative pressure vessel through a connecting tube, and the direction of the second check valve is from the inside of the tube body to the connecting tube.

The aseptic centrifuge tube further comprises a second cover body, the second cover body is threadedly connected with the first cover body, and a second sealing gasket is arranged between the second cover body and the first check valve and the second check valve.

The tube body is in a test tube shape, the first cover body is threadedly connected with the tube body, and a first sealing gasket is arranged between the tube body and the first cover body.

A tube cavity is arranged inside a wall surface of the catheter, the tube cavity extends along an axis direction of the catheter, a wall surface of the front end of the catheter is provided with a second through hole, the second through hole is connected with the tube cavity, the back end of the catheter is connected with a third branch tube, and the third branch tube is connected with the tube cavity.

The end of the third branch tube is connected with a third negative pressure vessel, and the third branch tube is provided with a third valve.

The first through hole is arranged in the middle of the guide part, the end of the piston part near the guide part is provided with a protruding sealing part, the sealing part is used to be plugged in the first through hole to seal the first through hole, a front end of the sealing part is of a circular arc shape with a smooth transition with the guide part.

One of an outer circumference of the sealing part and an inner circumference of the first through hole is arranged with an annular protruding part, the other one of the outer circumference of the sealing part and the inner circumference of the first through hole is arranged with a circular concave part, and the protruding part is matched with the concave part.

An outer wall of the catheter is provided with a length scale, and the zero point of the length scale is at the front end of the catheter.

An annular limit part is arranged in an inner circumference of the back end of the catheter, and the limit part is used to block the piston part, and the traction rope passes through the annular limit part.

The first branch tube is provided with a third check valve, the third check valve is close to the catheter, the direction of the third check valve is from the inside of the catheter to the first branch tube, the first valve is located between the third check valve and the first negative pressure vessel; and the connecting tube is provided with a fourth valve.

The beneficial effects of the present disclosure are: the circular arc-shaped guide part is arranged at the front end of the catheter to facilitate the insertion of the catheter into the bladder, and the piston part is arranged inside the front end of the catheter to seal the first through hole, so that there is no air in the front end of the catheter which prevents the air inside the front end of the catheter from contacting with the internal environment of the bladder and urine after the catheter is inserted into the bladder and affects the quality of sampling; after the catheter is inserted into the bladder, the piston part can be pulled back by the traction rope; with the pulling of the piston part, the urine in the bladder can be drained outward until the piston part passes the connection position of the first branch tube and the catheter, so that the catheter is communicated with the first branch tube; at this time, the first valve can be opened, so that the urine that flows out at beginning flows into the first negative pressure vessel under the negative pressure action of the first negative pressure vessel; this can not only help to remove the remaining bubbles due to the insertion of the catheter and the remaining bubbles in the catheter and avoid adverse effects on the anaerobic collection, but also discharge the gas caused by inflammation or other lesions in the bladder; when there is no bubble in the catheter, the first valve can be closed, and the second valve can be opened at this time; the negative pressure of the second negative pressure vessel can produce negative pressure in the aseptic centrifuge tube, and then make the urine in the catheter enter the aseptic centrifuge tube to realize the anaerobic collection of urine. After collecting the urine, the second negative pressure vessel and the second branch tube are removed from the aseptic centrifuge tube, and then the aseptic centrifuge tube containing the urine can be removed for the bacteria culture. The integrated urine anaerobic collection and culture apparatus maintains the anaerobic operating environment throughout the process from inserting the catheter into the bladder to the bacteria culture in the aseptic centrifuge tube, so the survival of the anaerobic bacteria is ensured to the maximum limit, and the accuracy of sampling and culturing the samples is improved. Moreover, the integrated urine anaerobic collection and culture apparatus has a simple structure and a low manufacturing cost. It has no electrical measuring instrument or driving equipment, and the operation is also very convenient.

Preferably, after the urine collection is completed and the aseptic centrifuge tube is removed, the second cover body is threaded on the outside of the first cover body tightly, and the second sealing gasket is pressed by the outer ends of the first check valve and the second check valve to achieve the sealing of the first check valve and the second check valve. Thus, even during a centrifuge operation, it can ensure that the aseptic centrifuge tube is in a closed state to avoid accidental opening of the first check valve and/or the second check valve during the centrifuge operation which allows air to enter the aseptic centrifuge tube.

Preferably, the first sealing gasket is arranged in the first cover body, and when the first cover body is screwed tightly on the tube body, the first sealing gasket is pressed by the end surface of the tube body to realize the sealing connection between the first cover body and the tube body.

Preferably, after the catheter is inserted into the bladder, the tube cavity communicates with the inner space of the bladder through the second through hole. After the catheter is inserted in place, urine can flow out through the second through hole and through the tube cavity, so that an operator can clearly see the urine, and then judge whether the catheter is inserted in place in the bladder.

Preferably, the third negative pressure vessel is connected to the tube cavity through the third branch tube, which can not only draw out the air in the tube cavity as much as possible through the opening of the third valve after the catheter is inserted into urethra, but also provide a negative pressure to the tube cavity to avoid slow or difficult urine discharge due to the small inner diameter of the tube cavity. After the catheter is inserted in place and a user observes urine flowing out of the tube cavity, the third valve is closed.

Preferably, a sealing part is arranged at the front end of the piston part. In an initial state, the sealing part is inserted into the first through hole, and the front end of the piston part is in contact with the inner surface of the guide part, so that there is no air inside either the first through hole or the front end of the catheter. When in use, with the backward movement of the piston part, the sealing part exits from the first through hole and the first through hole is opened, and the urine can enter the catheter and flow backward.

Preferably, the annular protruding part and the circular concave part form an embedded fitting to limit the sealing part and avoid the accidental backward movement of the sealing part and the piston part during the process of inserting the catheter into the bladder.

Preferably, a length scale is set on the outer wall of the catheter, so that the user can observe an insertion depth of the catheter and determine whether the catheter is inserted in place.

Preferably, the limit part is used to block the piston part. If the operator pulls the traction rope to drive the piston part to move for urine drainage, when the piston part is pulled in place, the limit part limits of the piston part to prevent the piston part from escaping from the catheter and external air from entering the catheter.

Preferably, the third check valve is arranged so that urine can only flow into the first negative pressure vessel without backflow.

BRIEF DESCRIPTION OF THE DRAWINGS

These and other purposes, features, and advantages of the present disclosure will become more apparent by a more detailed description of exemplary embodiments of the present disclosure in conjunction with the accompanying drawings, wherein the same reference label usually represents the same part in the exemplary embodiments of the present disclosure.

Explanation of reference numbers are as follows: 1. catheter; 2. guide part; 3. first through hole; 4. piston part; 5. traction rope; 6. first branch tube; 7. second branch tube; 8. first negative pressure vessel; 9. first valve; 10. second valve; 11. aseptic centrifuge tube; 12. tube body; 13. first cover body; 14. first check valve; 15. second check valve; 16. second negative pressure vessel; 17. connecting tube; 18. fourth valve; 19. third check valve; 20. limit part; 21. sealing part; 22. protruding part; 23. concave part; 24. first sealing gasket; 25. second sealing gasket; 26. tube cavity; 27. second through hole; 28. third branch tube; 29. third negative pressure vessel; 30. third valve; 31. second cover body.

DESCRIPTION OF THE EMBODIMENTS

Preferred embodiments of the present disclosure are described in more detail below. Although the preferred embodiments of the present disclosure are described below, it should be understood that the present disclosure may be implemented in various forms and should not be limited by the embodiments set forth herein. Rather, these embodiments are provided in order to make the present disclosure more thorough and complete, and to enable the complete communication of the scope of the present disclosure to a person skilled in the art.

Figure 1:
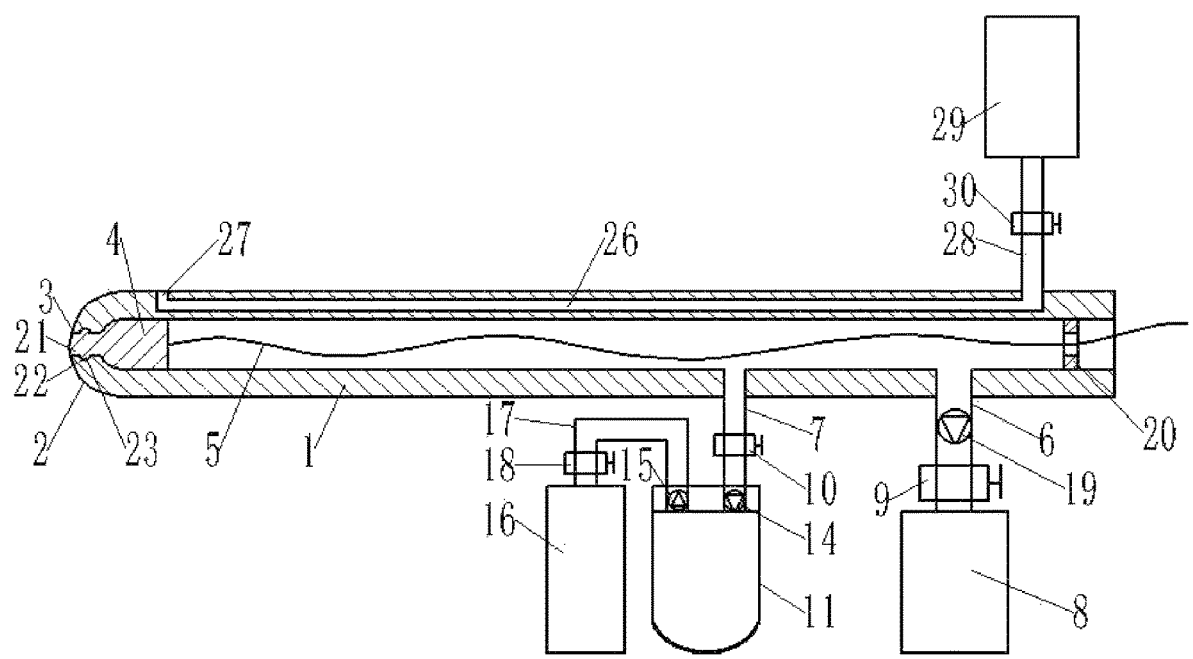
FIG. 1 is a structural diagram of an integrated urine anaerobic collection and culture apparatus of an embodiment of the present disclosure.
Figure 2:
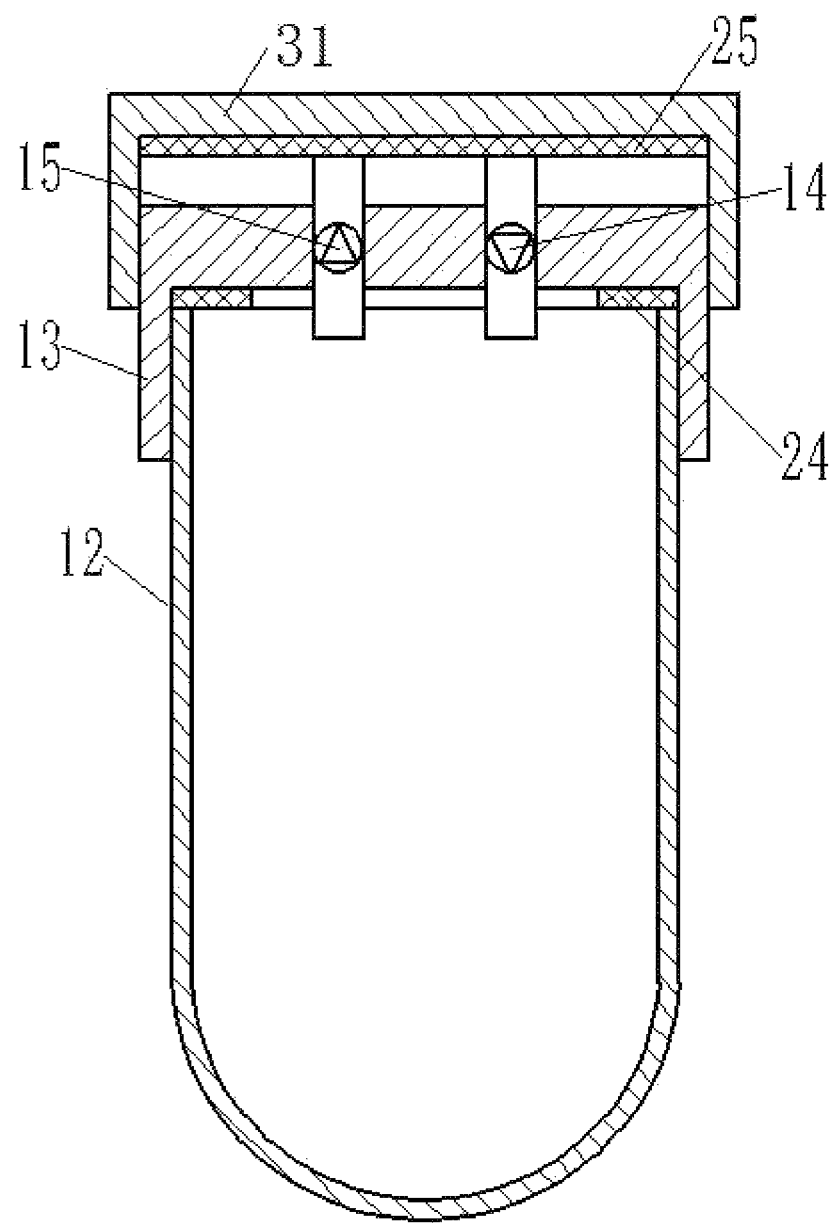
FIG. 2 is a structural diagram of an aseptic centrifuge tube in FIG. 1.

As shown in FIG. 1 and FIG. 2, provided in the present disclosure is an integrated urine anaerobic collection and culture apparatus, wherein the apparatus comprises a catheter 1, a front end of the catheter 1 is used to be inserted into a bladder, the front end of the catheter 1 is provided with a circular arc-shaped guide part 2, the front end of the catheter 1 is provided with a first through hole 3 communicated with the interior thereof, a piston part 4 is arranged inside the front end of the catheter 1, the piston part 4 is used to seal the first through hole 3, an end of the piston part 4 near the guide part 2 is in contact with the guide part 2, so that the front end of the piston part 4 is sealed with the guide part 2 with no gap therebetween, the outer circumference of the piston part 4 is fitted with an inner wall of the catheter 1 in a sliding seal manner, an end of the piston part 4 away from the guide part 2 is connected with a traction rope 5, and the traction rope 5 is threaded through the back end of the catheter 1. In this embodiment, the front end of the piston part 4 is a circular arc corresponding to the inner surface of the guide part 2. In this embodiment, the material of catheter 1 is latex, its length is 50-60 cm, the outer diameter of catheter 1 is 3-8 mm, and the thickness of the wall of catheter is 0.5 mm. The catheter 1 is inserted into the bladder through urethra of a human body, about 17-22 cm for males and 4-5 cm for females. Therefore, the length of the catheter between the front end of the catheter and the second branch tube can be set according to gender, which can be 25 cm for males and 8 cm for females.

A middle and back end of catheter 1 is connected with a first branch tube 6 and a second branch tube 7, and the first branch tube 6 and the second branch tube 7 are internally communicated with the catheter 1, and a connection position of the second branch tube 7 and the catheter 1 is located upstream of a connection position of the first branch tube 6 and the catheter 1, the first branch tube 6 is connected with a first negative pressure vessel 8, the first branch tube 6 and the second branch tube 7 are respectively provided with a first valve 9 and a second valve 10.

The first branch tube 6 is provided with a third check valve 19, the third check valve 19 is close to the catheter 1, the direction of the third check valve 19 is from the inside of the catheter 1 to the first branch tube 6, the first valve 9 is located between the third check valve 19 and the first negative pressure vessel 8. The third check valve 19 is arranged so that urine can only flow into the first negative pressure vessel 8 without backflow.

The second branch tube 7 is connected with an aseptic centrifuge tube 11, the aseptic centrifuge tube 11 comprises a tube body 12 and a first cover body 13, the first cover body 13 is provided with a first check valve 14 and a second check valve 15, wherein the first check valve 14 is connected with the second branch tube 7, the direction of the first check valve 14 is from the second branch tube 7 to the inside of the tube body 12, the second check valve 15 is connected with a second negative pressure vessel 16 through a connecting tube 17, and the direction of the second check valve 15 is from the tube body 12 to the connecting tube 17. The connecting tube 17 is provided with a fourth valve 18. Alternatively, the first negative pressure vessel 8 and the second negative pressure vessel 16 can be negative pressure bottles, negative pressure tubes or negative pressure bags.

In this embodiment, when the first cover body 13 seals the orifice of the tube body 12, one end of the first check valve 14 and the second check valve 15 is communicated with the internal space of the tube body 12, and the other end of the first check valve 14 and the second check valve 15 are detachable connected with the second branch tube 7 and the second negative pressure vessel 16 respectively. The detachable connection may be either a plug-and-pull connection or a threaded connection.

In the integrated urine anaerobic collection and culture apparatus of the present disclosure, the circular arc-shaped guide part 2 is arranged at the front end of the catheter 1 to facilitate the insertion of the catheter 1 into the bladder, and the piston part 4 is arranged inside the front end of the catheter 1 to seal the first through hole 3, so that there is no air in the front end of the catheter 1 which prevents the air inside the front end of the catheter 1 from contacting with the internal environment of the bladder and urine after the catheter is inserted into the bladder and affects the quality of sampling; after the catheter 1 is inserted into the bladder, the piston part 4 can be pulled back by the traction rope 5; with the pulling of the piston part 4, the urine in the bladder can be drained outward until the piston part 4 passes the connection position of the first branch tube 6 and the catheter 1, so that the catheter 1 is communicated with the first branch tube 6; at this time, the first valve 9 can be opened, so that the urine that flows out at beginning flows into the first negative pressure vessel 8 under the negative pressure action of the first negative pressure vessel 8; this can not only help to remove the remaining bubbles due to the insertion of the catheter 1 and the remaining bubbles in the catheter 1 and avoid adverse effects on the anaerobic collection, but also discharge the gas caused by inflammation or other lesions in the bladder; when there is no bubble in the catheter 1, the first valve 9 can be closed, and the second valve 10 can be opened at this time; the negative pressure of the second negative pressure vessel 16 can produce negative pressure in the aseptic centrifuge tube 11, and then make the urine in the catheter 1 enter the aseptic centrifuge tube 11 to realize the anaerobic collection of urine. After collecting the urine, the second negative pressure vessel 16 and the second branch tube 7 are removed, and then the aseptic centrifuge tube 11 containing the urine can be removed for the bacteria culture. The integrated urine anaerobic collection and culture apparatus maintains the anaerobic operating environment throughout the process from inserting the catheter 1 into the bladder to the bacteria culture in the aseptic centrifuge tube 11, so the survival of the anaerobic bacteria is ensured to the maximum limit, and the accuracy of sampling and culturing the samples is improved. Moreover, the integrated urine anaerobic collection and culture apparatus has a simple structure and a low manufacturing cost. It has no electrical measuring instrument or driving equipment, and the operation is also very convenient.

In the aseptic centrifuge tube of this embodiment, the tube body 12 is in a test tube shape, the first cover body 13 is threadly connected with the tube body 12, and a first sealing gasket 24 is arranged between the tube body 12 and the first cover body 13. The aseptic centrifuge tube 11 further comprises a second cover body 31, the second cover body 31 is threadly connected with the first cover body 13, and a second sealing gasket 25 is arranged between the second cover body 31 and the first check valve 14 and the second check valve 15.

The first sealing gasket 24 is arranged in the first cover body 13, and when the first cover body 13 is screwed tightly on the tube body 12, the first sealing gasket 24 is pressed by the end surface of the tube body 12 to realize the sealing connection between the first cover body 13 and the tube body 12. The second sealing gasket 25 is arranged in the second cover body 31. When the aseptic centrifuge tube 11 needs to be removed after urine collection is completed, the second branch tube 7 and the second negative pressure vessel 16 on the first check valve 14 and the second check valve 15 are removed. When the second cover body 31 is threaded on the outside of the first cover body 13 tightly, the second sealing gasket 25 is pressed by the outer ends of the first check valve 14 and the second check valve 15 to achieve the sealing of the first check valve 14 and the second check valve 15. Thus, even during a centrifuge operation, it can ensure that the aseptic centrifuge tube 11 is in a closed state to avoid accidental opening of the first check valve 14 and/or the second check valve 15 during the centrifuge operation which allows air to enter the aseptic centrifuge tube 11. A tube cavity 26 is arranged inside a wall surface of the catheter 1, the tube cavity 26 extends along an axis direction of the catheter 1, a wall surface of the front end of the catheter 1 is provided with a second through hole 27, the second through hole 27 is connected with the tube cavity 26, the back end of the catheter 1 is connected with a third branch tube 28, and the third branch tube 28 is connected with the tube cavity 26. The end of the third branch tube 28 is connected with a third negative pressure vessel 29, and the third branch tube 28 is provided with a third valve 30.

Specifically, the tube cavity 26 is arranged along the axis of catheter 1, which can be a thin tube embedded in the side wall of catheter 1, or a tubular cavity directly arranged in the side wall of catheter 1. After the catheter 1 is inserted into the bladder, the tube cavity 26 communicates with the inner space of the bladder through the second through hole 27. After the catheter 1 is inserted in place, urine can flow out through the second through hole 27 and through the tube cavity 26, so that an operator can clearly see the urine, and then judge whether the catheter 1 is inserted in place in the bladder. The third negative pressure vessel 29 is connected to the tube cavity 26 through the third branch tube 28, which can not only draw out the air in the tube cavity 26 as much as possible through the opening of the third valve 30 after the catheter 1 is inserted into urethra, but also provide a negative pressure to the tube cavity 26 to avoid slow or difficult urine discharge due to the small inner diameter of the tube cavity 26. After the catheter 1 is inserted in place and a user observes urine flowing out of the tube cavity 26, the third valve 30 is closed.

The first through hole 3 is arranged in the middle of the guide part 2, an end of the piston part 4 near the guide part 2 is provided with a protruding sealing part 21, the sealing part 21 is used to be plugged in the first through hole 3 to seal the first through hole 3, a front end of the sealing part 21 is a of a circular arc shape with a smooth transition with the guide part 2. One of an outer circumferences of the sealing part 21 and an inner circumference of the first through hole 3 is arranged with an annular protruding part 22, the other one of the outer circumference of the sealing part 21 and the inner circumference of the first through hole 3 is arranged with a circular concave part 23, and the protruding part 22 is matched with the concave part 23.

Specifically, the first through hole 3 may be arranged in the middle of the guide part 2 along the axis of the catheter 1 and communicated with the internal space of the catheter 1. In an initial state, the sealing part 21 is inserted into the first through hole 3, and the front end of the piston part 4 is in contact with the inner surface of the guide part 2, so that there is no air inside either the first through hole 3 or the front end of the catheter 1. When in use, with the backward movement of the piston part 4, the sealing part 21 exits from the first through hole 3 and the first through hole 3 is opened, and the urine can enter the catheter 1 and flow backward.

In this embodiment, the protruding part 22 is arranged on the outer circumference of the sealing part 21, and the concave part 23 is arranged on the inner circumference of the first through hole 3. Specifically, the annular protruding part 22 and the circular concave part 23 form an embedded fitting to limit the sealing part 21 and avoid the accidental backward movement of the sealing part 21 and the piston part 4 during the process of inserting the catheter 1 into the bladder.

An outer wall of the catheter 1 is provided with a length scale, and the zero point of the length scale is at the front end of the catheter 1.

The length scale can be in millimeter as the smallest unit. The length scale is set so that the user can observe an insertion depth of the catheter 1 and determine whether the catheter 1 is inserted in place.

An annular limit part 20 is arranged in an inner circumference of the back end of the catheter 1, and the limit part 20 is used to seal the piston part 4, and the traction rope passes through the annular limit part. If the traction rope 5 passes through the inside of the limit part 20 and extends outwards so that the operator can pull the traction rope 5 to drive the piston part 4 to move for urine drainage, when the piston part 4 is pulled in place, the limit part 20 limits of the piston part to prevent the piston part from escaping from the catheter 1 and external air from entering the catheter 1.

In other embodiments of the present disclosure, the first through hole 3 on the catheter 1 may be opened on the guide part 2 or on the side wall of catheter 1 near the end of guide part 2, and the piston part 4 is arranged to seal the first through hole 3 and to allow the catheter 1 to be inserted into the bladder through the urethra with as little air as possible.

Embodiments of the present disclosure have been described above, which are exemplary, not exhaustive, and are not limited to the embodiments disclosed. Without departing from the scope and spirit of the embodiments illustrated, many modifications and changes are apparent to an ordinary skilled person in the technical field.

What is claimed is:

1. An integrated urine anaerobic collection and culture apparatus, wherein the apparatus comprises a catheter, a front end of the catheter is used to be inserted into a bladder, a middle and back end of the catheter is connected with a first branch tube and a second branch tube, the front end of the catheter is provided with a circular arc-shaped guide part, the front end of the catheter is provided with a first through hole communicated with the interior thereof, a piston part is arranged inside the front end of the catheter, the piston part is used to seal the first through hole, an end of the piston part near the guide part is in contact with the guide part, so that a front end of the piston part is sealed with the guide part with no gap therebetween, an outer circumference of the piston part is fitted with an inner wall of the catheter in a sliding seal manner, an end of the piston part away from the guide part is connected with a traction rope, and the traction rope passes through the back end of the catheter; the first branch tube and the second branch tube are internally connected with the catheter, and a connection position of the second branch tube and the catheter is located upstream of a connection position of the first branch tube and the catheter, the first branch tube is connected with a first negative pressure vessel, the first branch tube and the second branch tube are respectively provided with a first valve and a second valve; the second branch tube is connected with an aseptic centrifuge tube, the aseptic centrifuge tube comprises a tube body and a first cover body, wherein the first cover body is provided with a first check valve and a second check valve, the first check valve is connected with the second branch tube, a direction of the first check valve is from the second branch tube to an inside of the tube body, the second check valve is connected with a second negative pressure vessel through a connecting tube, and a direction of the second check valve is from the inside of the tube body to the connecting tube; the first through hole is arranged in middle of the guide part, the end of the piston part near the guide part is provided with a protruding sealing part, the sealing part is used to be plugged in the first through hole to seal the first through hole, a front end of the sealing part is of a circular arc shape with a smooth transition with the guide part; one of an outer circumference of the sealing part and an inner circumference of the first through hole is arranged with an annular protruding part, the other one of the outer circumference of the sealing part and the inner circumference of the first through hole is arranged with an annular concave part, and the protruding part is matched with the concave part; an annular limit part is arranged in an inner circumference of the back end of the catheter, and the limit part is used to block the piston part, and the traction rope passes through the annular limit part; the first branch tube is provided with a third check valve, the third check valve is close to the catheter, a direction of the third check valve is from an inside of the catheter to the first branch tube, the first valve is located between the third check valve and the first negative pressure vessel; and the connecting tube is provided with a fourth valve.

2. The integrated urine anaerobic collection and culture apparatus according to claim 1, wherein the aseptic centrifuge tube further comprises a second cover body, the second cover body is threadedly connected with the first cover body, and a second sealing gasket is arranged between the second cover body and the first check valve and the second check valve.

3. The integrated urine anaerobic collection and culture apparatus according to claim 1, wherein the tube body is in a test tube shape, the first cover body is threadedly connected with the tube body, and a first sealing gasket is arranged between the tube body and the first cover body.

4. The integrated urine anaerobic collection and culture apparatus according to claim 1, wherein a tube cavity is arranged inside a wall surface of the catheter, the tube cavity extends along an axis direction of the catheter, a wall surface of the front end of the catheter is provided with a second through hole, the second through hole is connected with the tube cavity, the back end of the catheter is connected with a third branch tube, and the third branch tube is connected with the tube cavity.

5. The integrated urine anaerobic collection and culture apparatus according to claim 4, wherein an end of the third branch tube is connected with a third negative pressure vessel, and the third branch tube is provided with a third valve.

6. The integrated urine anaerobic collection and culture apparatus according to claim 1, wherein an outer wall of the catheter is provided with a length scale, and a zero point of the length scale is at the front end of the catheter.

* * * * *